US010575924B2

(12) United States Patent
Guaragno (10) Patent No.: US 10,575,924 B2
(45) Date of Patent: Mar. 3, 2020

(54) ULTRASONIC DENTAL HANDPIECE WITH ROTARY COUPLING

(71) Applicant: DENTSPLY SIRONA Inc., York, PA (US)

(72) Inventor: Kenneth R Guaragno, Spring Grove, PA (US)

(73) Assignee: DENTSPLY SIRONA INC., York, PA (US)

( * ) Notice: Subject to any disclaimer, the term of this patent is extended or adjusted under 35 U.S.C. 154(b) by 0 days.

(21) Appl. No.: 15/785,475

(22) Filed: Oct. 17, 2017

(65) Prior Publication Data

US 2018/0104021 A1    Apr. 19, 2018

Related U.S. Application Data

(60) Provisional application No. 62/409,120, filed on Oct. 17, 2016.

(51) Int. Cl.
*A61C 1/18* (2006.01)
*A61C 17/02* (2006.01)
*A61C 17/20* (2006.01)

(52) U.S. Cl.
CPC .............. *A61C 1/188* (2013.01); *A61C 17/02* (2013.01); *A61C 17/20* (2013.01)

(58) Field of Classification Search
CPC ........... A61C 1/188; A61C 1/07; A61C 17/02; A61C 17/20
USPC ............................................................ 433/86
See application file for complete search history.

(56) References Cited

U.S. PATENT DOCUMENTS

| 9,050,161 | B2 | 6/2015 | Feine |
| 9,707,050 | B2 | 7/2017 | Guaragno |
| 2002/0127512 | A1 | 9/2002 | Chen |
| 2003/0022129 | A1 | 1/2003 | Rahman |

(Continued)

FOREIGN PATENT DOCUMENTS

WO    20090117464 A1    9/2009

OTHER PUBLICATIONS

International Search Report; PCT/US2017/056841; Dec. 15, 2017 (Completed); dated Jan. 4, 2018.

(Continued)

*Primary Examiner* — Matthew M Nelson
(74) *Attorney, Agent, or Firm* — Dentsply Sirona Inc.

(57) ABSTRACT

An ultrasonic dental handpiece system with rotary coupling comprising a dental handpiece and a dental handpiece tip wherein the system incorporates a swivel mechanism and dynamic fluid interface for the dental handpiece and dental handpiece tip to rotate freely relative to the dental handpiece cable thereby decoupling the handpiece from a torsion load applied to it by the handpiece cable and internal tubing and wires. The ultrasonic dental handpiece with rotary coupling generally includes a handpiece to which a piezo assembly and secondary coil are housed and a cable assembly including a primary coil and handpiece cable wherein the handpiece cable provides a supply of electrical energy and cooling lavage. The primary and secondary coils form a transformer wherein the secondary coil is inductively coupled to the primary coil with the secondary coil in electrical communication with the piezo assembly. A method of using a handpiece is also disclosed.

11 Claims, 13 Drawing Sheets

(56) References Cited

U.S. PATENT DOCUMENTS

| | | | | |
|---|---|---|---|---|
| 2011/0269102 A1* | 11/2011 | Kuhn | ................... | A61C 1/06 |
| | | | | 433/131 |
| 2014/0356810 A1* | 12/2014 | Novak | ................... | A61C 1/141 |
| | | | | 433/127 |
| 2015/0333535 A1* | 11/2015 | Feine | ................... | A61C 17/20 |
| | | | | 307/104 |

OTHER PUBLICATIONS

Written Opinion of the International Searching Authority; PCT/US2017/056841; Dec. 15, 2017 (Completed); dated Jan. 4, 2018.
International Preliminary Report on Patentability; PCT/US2017/056841; Dec. 5, 2017 (Completed); dated Jan. 4, 2018.

* cited by examiner

ULTRASONIC DENTAL HANDPIECE WITH ROTARY COUPLING

FIELD OF THE INVENTION

The present invention relates generally to dental handpieces and more specifically to an ultrasonic dental handpiece assembly with rotary coupling and a fluid transmission mechanism for providing the handpiece assembly with energy and cooling lavage.

BACKGROUND OF THE INVENTION

An ultrasonic dental tool typically includes a handpiece connected to a cable that connects both electrical power, ground, and feedback circuits. The cable may include a flexible tube to provide lavage (e.g., water, Chlorohexidine, mouth wash). Currently clinicians must maintain a tight grip on ultrasonic scalers in order to maintain an appropriate scaler tip orientation relative to tooth surfaces during ultrasonic cleaning procedures. This is due to the fact that piezo tips are attached to the handpiece using a threaded connection, as a result the tips orientation relative to the cable assembly is rigidly fixed to the horn of the transducer and handpiece housing. The tips orientation is dependent on thread timing and is independent of the direction of that the cable is draped. The rigid nature of the handpiece and tip assembly prevents the rotation of the handpiece to properly orient the tip of the handpiece to the tooth surface without corresponding torsional drag being transmitted from the handpiece cable and internal tubing and wiring to the gripping region. The problem has been recognized by U.S. patent application Ser. No. 14/716,075 which discloses a magnetostrictive handpiece comprising an inner barrel, a coil unit and an outer sheath wherein a rotatable nozzle is selectively rotatable in response to an application of a torsional load to a grip region. It is hereby incorporated by reference for background purposes. U.S. Pat. No. 9,050,161 expands the functionality of a magnetostrictive generator by making it compatible with piezo style tips. However the problem remains to be solved using piezoelectric technology. A dental handpiece, a dental system including a dental handpiece and a method of using said dental handpiece that shows one or more improvements in comparison with prior art is desired in the art.

BRIEF SUMMARY OF THE INVENTION

The system comprises a dental handpiece, dental handpiece tip and a cable assembly wherein the handpiece incorporates a dynamic fluid interface and a swivel mechanism that allows the handpiece and handpiece tip to rotate freely relative to a handpiece cable or user's hand while unrestrictedly transmitting energy and lavage inside the handpiece through the decoupling of the handpiece from a torsion load applied to it by the handpiece cable and internal tubing and wires. The handpiece houses a piezo stack and a secondary coil, and the cable assembly comprises a cable (cable sheath, tubing, and wires) and a primary coil, the cable providing a supply of electrical energy and cooling lavage to the handpiece. The primary and secondary coils form a transformer with the secondary coil inductively coupled to the primary coil and with the secondary coil in electrical communication with said piezo stack. By avoiding the need to precisely align commutating electrical contacts, it is possible for the handpiece rotation mechanism to be made from low friction materials without the need for bearings or other precision components. A ferrite core underneath the primary coil concentrates the flux to increase coupling with the secondary coil and to allow for the efficient transfer of power. A dynamic fluid interface and a swivel mechanism allow the handpiece and handpiece tip to rotate freely relative to a handpiece cable.

There has thus been outlined, rather broadly, some of the features of the invention in order that the detailed description thereof may be better understood, and in order that the present contribution to the art may be better appreciated. There are additional features of the invention that will be described hereinafter.

In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

An object is to provide an ultrasonic dental handpiece system with rotary coupling wherein the system comprises a dental handpiece and a dental handpiece tip, said system incorporating a swivel mechanism and a rotary fluid coupling to allow the handpiece and tip to rotate, preferably 360 degrees, relative to a handpiece cable thereby decoupling the handpiece from a torsion load applied to it by the cable and internal fluid tubing and electrical wires.

Another object is to provide an ultrasonic dental handpiece system with rotary coupling that may be used for general supra and subgingival scaling applications, endodontic procedures and for periodontal debridement for all types of periodontal diseases.

Another object is to provide an ultrasonic dental handpiece with rotary coupling that replaces conventional electrical connections by the use of a transformer, hereinafter referred to as a rotary transformer, to transfer ultrasonic power via electromagnetic coupling between a primary coil and a secondary coil. Two concentric shells nest inside each other protecting the coils from fluid ingress and contamination while creating an electromagnetic coupling used to drive the piezo handpiece. In addition, it is an object to adopt latching mechanisms to provide a means for making the handpiece easily detachable for sterilization and replacement, and to offer the capability of venting during autoclave cycles in addition to insensitivity to fluid ingress. The coil over coil design eliminates the need for commutating electrical contacts and hermetic radial seals that provide low friction slip coupling barrier to fluid and steam.

Other objects and advantages of the present invention will become obvious to the reader and it is intended that these objects and advantages are within the scope of the present invention. To the accomplishment of the above and related objects, this invention may be embodied in the form illustrated in the accompanying drawings, attention being called to the fact, however, that the drawings are illustrative only, and that changes may be made in the specific construction illustrated and described within the scope of this application.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

Turning descriptively to the drawings, in which similar reference characters denote similar elements throughout the several views, the figures illustrate a handpiece to which a piezo assembly and secondary coil are mechanically attached and housed and a cable assembly comprising a primary coil and handpiece cable wherein the handpiece cable provides a supply of electrical energy and cooling lavage. The primary and secondary coils form a transformer wherein the secondary coil is inductively coupled to the primary coil with the secondary coil in electrical communication with said piezo assembly. A ferrite core underneath the primary winding concentrates the flux to increase coupling with the secondary winding to allow for the efficient transfer of power. Each coil is sealed in its own shell to eliminate the risk for fluid entry that degrades electrical insulation between the user and the high voltage electrical connection. In an embodiment, an electrical circuit capable of characterizing the piezoelectric transducer over a multitude of operating frequencies through digitally controlled drive electronics is used. The drive circuitry is capable of digitally synthesizing a range of excitation frequencies while simultaneously monitoring drive voltage and current. The drive voltage and current are digitized via an analog to digital converter to provide a microcontroller with information such as phase relationship, impedance, admittance, and current draw. This information coupled with the excitation frequency is analyzed to determine the transducer's optimum operation frequency which will be at or near the resonant frequency of the transducer and attached tool. The drive voltage and current are dynamically controlled using pulse width modulation techniques based on user settings. Preferably the drive voltage and current approximate a sine wave in order to minimize unwanted harmonics that result in audible noise and transformer losses generating heat in the handpiece and potentially unwanted electromagnetic emissions.

Figure 1:
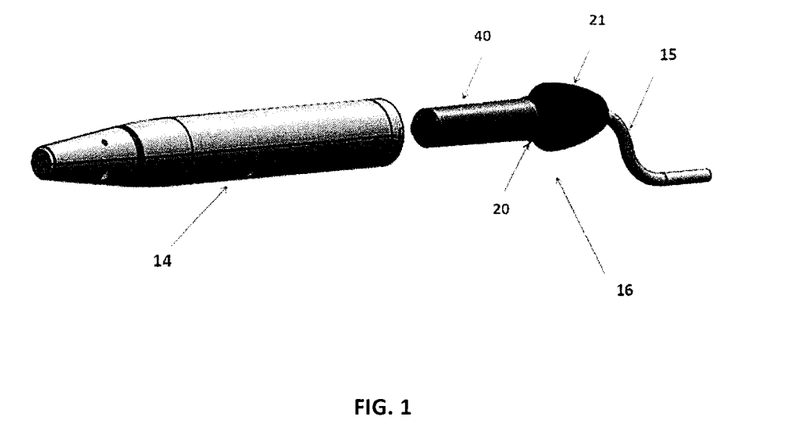
FIG. 1 is a perspective view illustrating a preferred embodiment of the disclosure.
Figure 4:
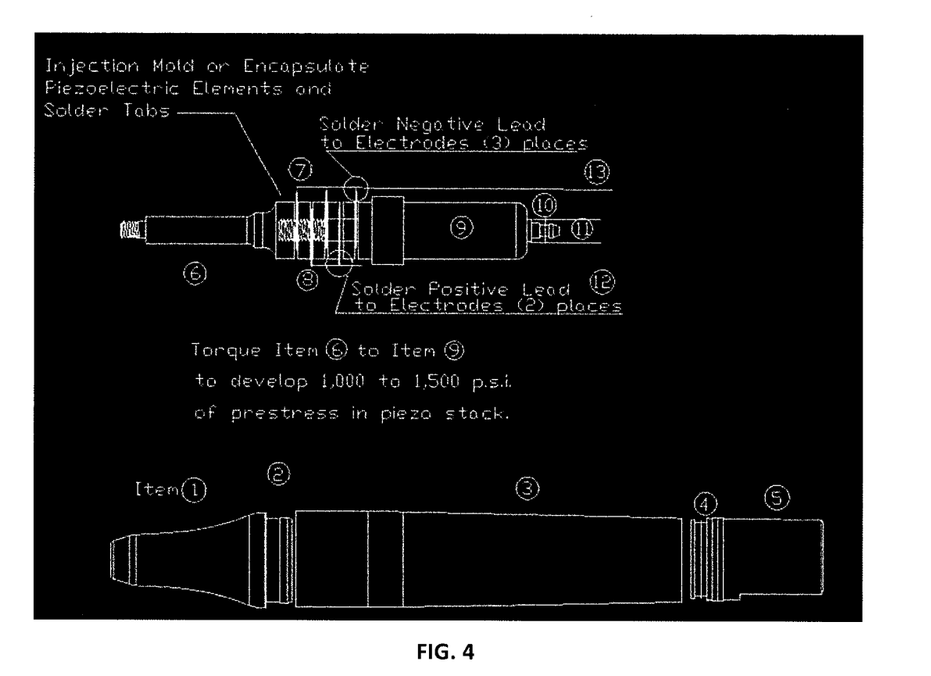
FIG. 4 illustrates the general components of a piezo ultrasonic scaling handpiece with a transducer.

Turning to FIG. 1, a piezo scaler handpiece 14 is uncoupled from cable assembly 16. The cable assembly is supplied with lavage and electrical energy through the handpiece cable 15. A primary coil coupling 40 protruding from one end of a rear cap 21, which is supplied with an O-ring 20, allows the scaler handpiece body 14 to rotate freely relative to the cable 15. Preferably, a scaler tip (not shown) is also able to rotate freely relative to the handpiece body through the adoption of O-rings 2 in the design of the handpiece housing tip 1 as shown in FIG. 4. The coupling arrangement allows the provision of power to a piezoelectric pile 8 coupled to a mechanical working end (not shown). The coupling also allows the provision of lavage through the body of the handpiece 14 to the mechanical working end (not shown) of the piezoelectric pile 8. The ability to uncouple the handpiece 14 from the primary coil coupling 40 allows mechanical and electrical integration of the components of the handpiece 14 such that it can be easily cleaned, and can resist fluid ingress and withstand high temperatures and pressures from autoclaving without any damage to internal components. This also allows a handpiece of size comparable to conventional dental handpieces to be created. The primary coil coupling 40 of the cable assembly 16 is a friction grip coupling. A Teflon bearing 19, in FIG. 2, resides in the in rear end of the handpiece. An O-ring 20 interlocks with the inside diameter of the Teflon bearing to secure the handpiece to the cable assembly. A primary coil protruding from the end of the cable assembly is delivered into the core of a secondary coil located in the handpiece. The turns ratio will normally be 1:1. Once the handpiece is fully seated onto the protruding primary coil and latched onto the handpiece, a low friction fluid coupling is joined between the handpiece and the cable assembly.

Figure 2:
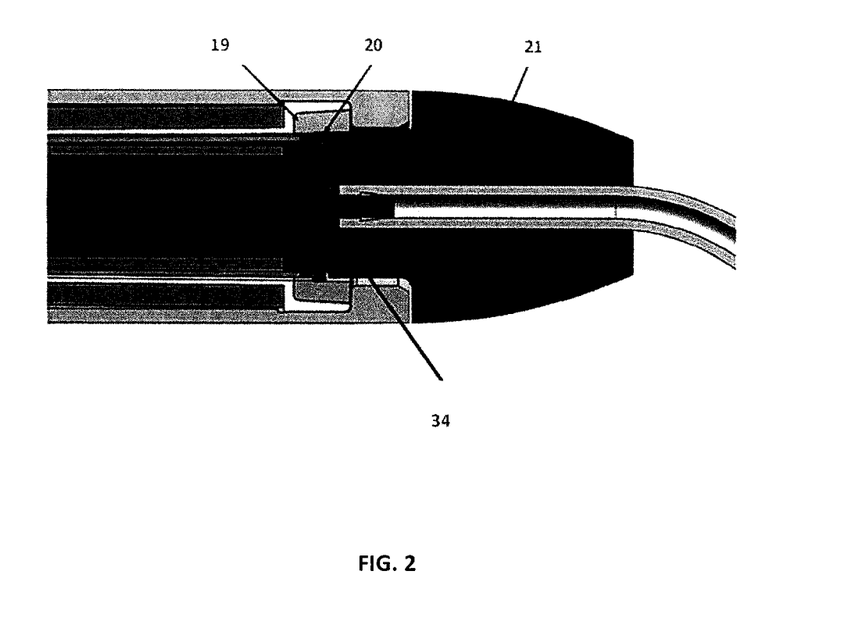
FIG. 2 is a cross sectional view of the rotational interface (cable assembly/handpiece connection) highlighting a smooth Teflon bearing about which rotation is executed.

Referring to FIG. 2 which illustrates a cross sectional view of the rotational interface (cable assembly/handpiece connection), the Teflon bearing 19 resides in the proximal end of the handpiece. An O-ring 20 of the cable assembly interlocks with the inside diameter of the Teflon bearing 19 to secure the handpiece to the cable assembly. A fluid channel of the handpiece cable 15 is connected to a fluid channel of a primary bobbin 31 through a primary washer 34. Lavage is directed through the fluid channels to the piezo assembly 23 to cool the ultrasonic scaling tip. In addition to supplying lavage, the cable 15 also supplies electrical energy, preferably through electrically insulated wires (not shown).

Figure 3:
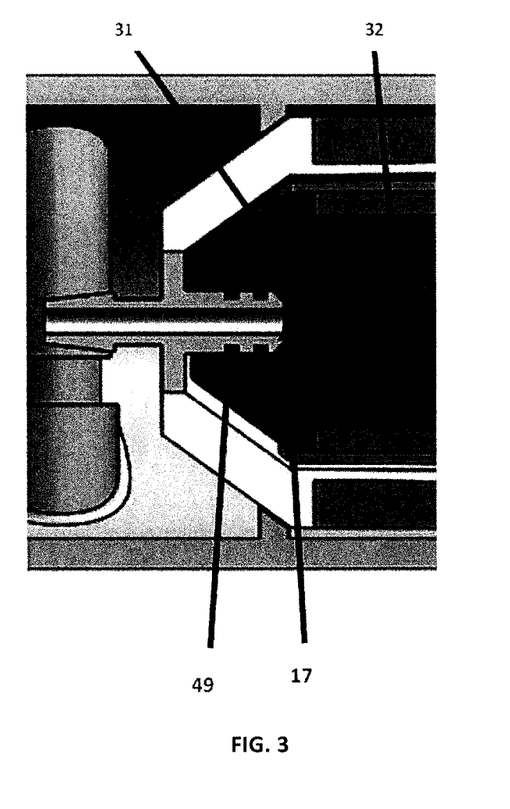
FIG. 3 is a cross sectional view of the cable assembly and handpiece connection highlighting a dynamic fluid interface according to the disclosure.
Figure 8:
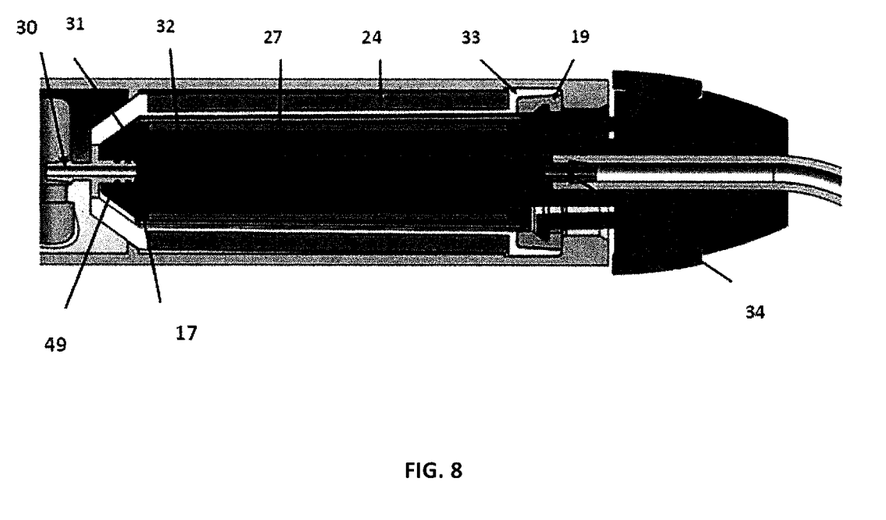
FIG. 8 is a cross sectional view of the alternative embodiment of FIG. 6 showing the cable assembly having a clip mechanism for connection with the proximal end of the handpiece.

Referring to FIG. 3 and FIG. 8, an interference fit between the dynamic fluid interface 17 and primary bobbin 31 of the primary coil 27 generates a force that results in frictional torque and consumes energy as the handpiece is rotated by the clinician. The correct functioning of the interface depends on maintaining a sealing force between the primary bobbin 31 and inside diameter of the dynamic fluid interface 17. In attempting to reduce the frictional torque generated from the force of the interference fit, an appropriate load, usually less than 7.06 mN.m (1 in-oz), and preferably less than 3.53 mN.m (½ in-oz), is maintained to prevent seal leakage and to guarantee a smoothly and freely rotatable handpiece that provides maximum control to achieve proper scaler tip orientation and adaptation to dental anatomy. This minimal torque will allow the clinician to rotate the insert with one hand, eliminating the need to leave the oral cavity to use both hands in order to reposition the tip. The amount of torque can be read directly from a torque watch as the handpiece is rotated relative to the cable. The O-rings' 49 ability to seal against the head pressure of an ultrasonic handpiece can be directly estimated by the peak contact stress of the o-ring. The radial load on the primary bobbin 31 will be negligible at the o-ring 49 because of the bearing, the feather like touch used during scaling, and the fact that the o-ring seal is located deep in the handpiece. The primary wall peak contact stress response for radial loading is the greatest as a result of o-ring deformation. The following equation is the calculation for the axial torque as a result of the seal's coefficient of friction ($\mu$), shaft radius(Rs), and axial loading (RL). Note that torque is directly proportional to the shaft radius.

Torque=$\mu$RsRL.

Figure 13:
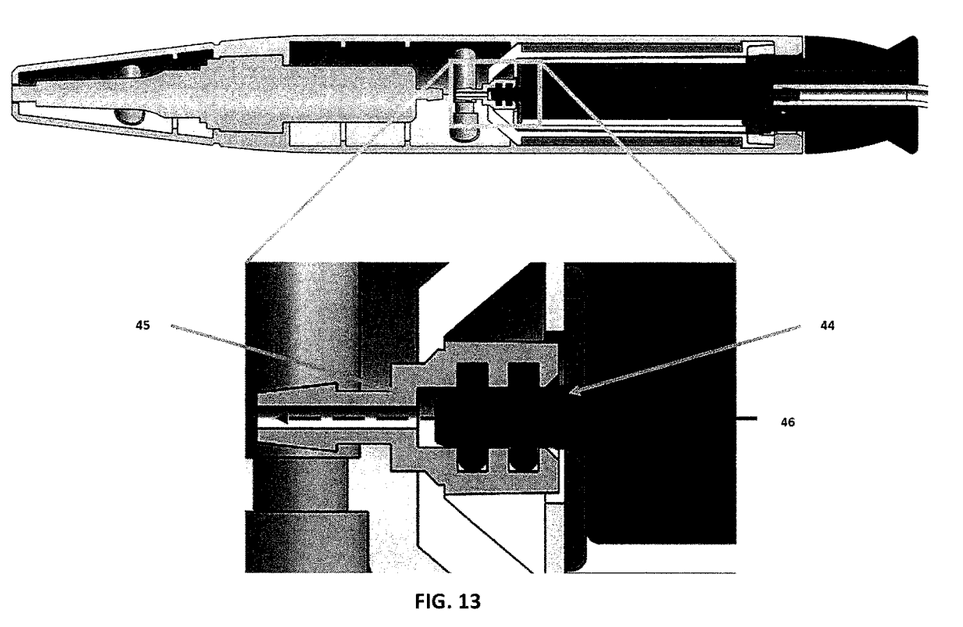
FIG. 13 shows an alternative embodiment of the dynamic fluid interface.

The o-ring stiffness, material, and shaft finish affects both the static and dynamic coefficient of friction. Care is taken such that the primary bobbin shaft surface finish is glass like and that any parting line flash is eliminated. O-ring stiffness and percent deformation directly controls radial load. Preferably, high temperature o-ring materials, such as Teflon, Teflon coated fluorocarbons, and high temperature silicone, are used to prevent swelling from moisture ingress or stiffening from a loss of plasticizers from the o-ring after repeated autoclave cycles. FIG. 13 shows an alternative embodiment of the dynamic fluid interface. This features low friction materials, smooth finish and a small radius giving the interface resilience to damage when the two halves are separated. Bobbin 44 moves with the cable and water fitting 45 moves with the handpiece 46 shows the direction of lavage flow.

Figure 5:
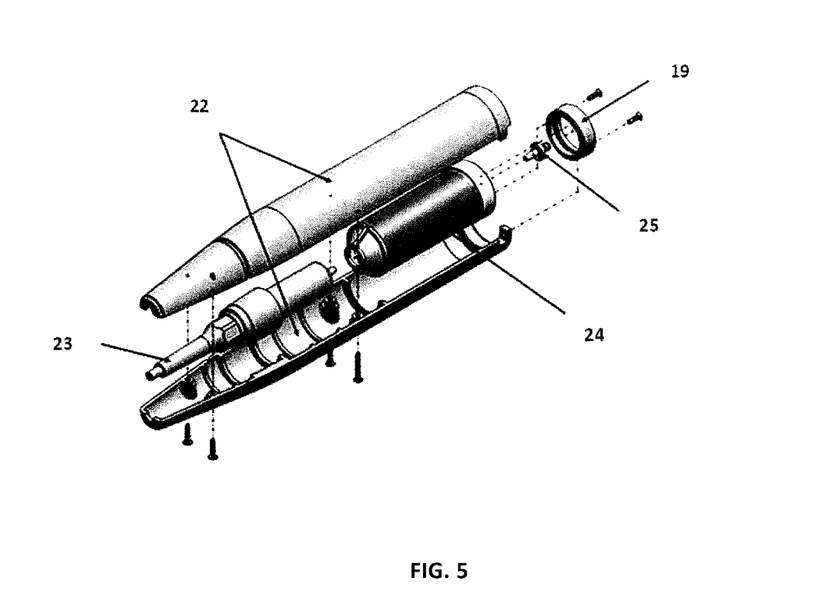
FIG. 5 illustrates an exploded view of the handpiece with the transducer and secondary coil in place.

FIG. 4 illustrates the general components of a piezo ultrasonic scaling handpiece with a transducer. The handpiece comprises a housing tip 1 and a housing 3. The housing 3 is connected to the housing tip 1 by the use of a housing tip O-ring 2. A connector O-ring 4 connects the housing to a connector 5 from which power is supplied to the transducer. The transducer is housed in the handpiece and comprises an ultrasonic horn 6, piezoelectric elements 8, solder tabs 7 that transfer electrical voltage to the surface of the piezo element, and a Tail Mass (or back mass) 9 with an o-ring 10 that when assembled forms a Langevin or metal sandwich transducer. A metal barb fluid fitting 11 provides a connection to deliver cooling lavage through the center of the transducer in order to cool the ultrasonic scaling tip. FIG. 5 illustrates an exploded view of the handpiece with the transducer 23 and secondary coil in place 24. The outer casework 22 consists of two shells fastened together by screws. A single shell or alternative bonding technique may be implemented to improve ease of cleaning and aesthetics.

Figure 6:
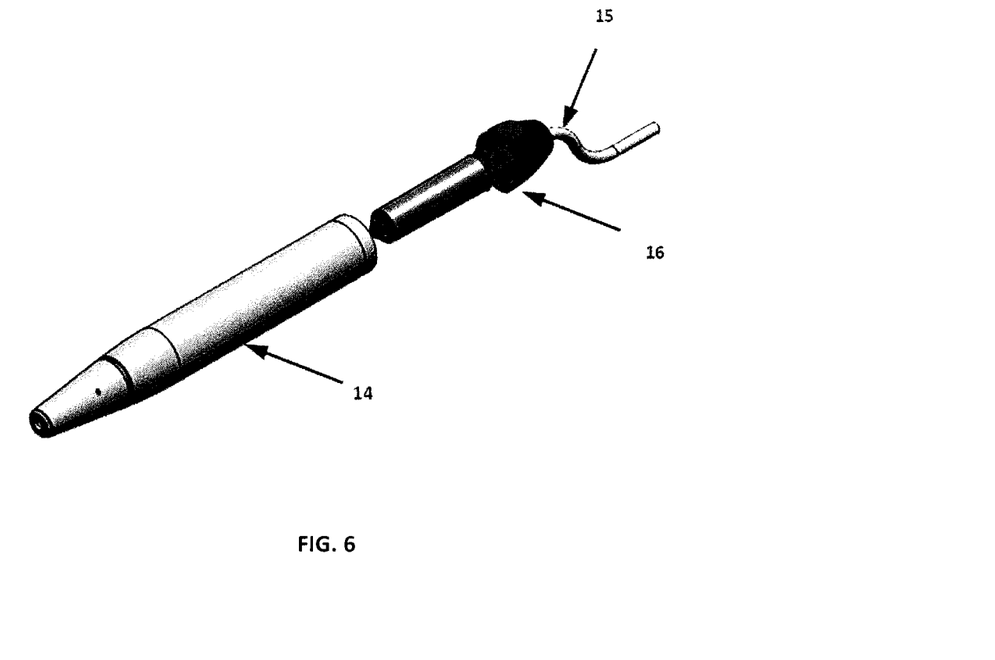
FIG. 6 illustrates a perspective view of an alternative embodiment of the invention. A cable assembly is provided with a clip mechanism to allow affixing of the cable assembly to the handpiece.
Figure 7:
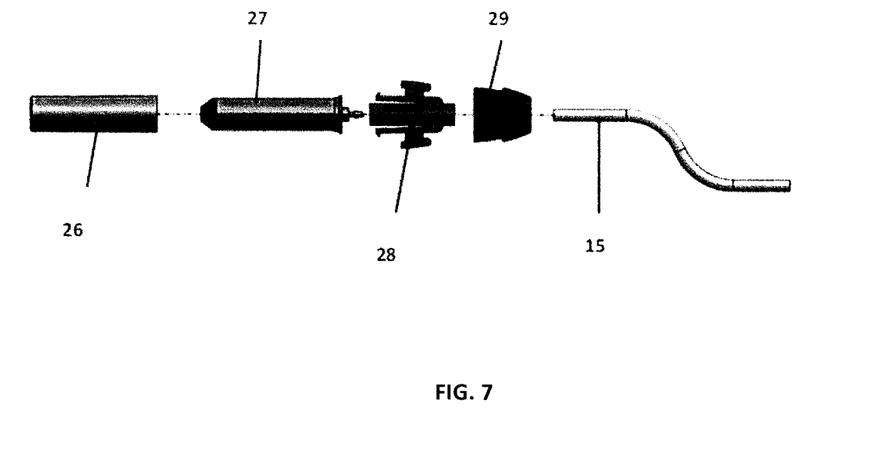
FIG. 7 shows an exploded side view of the cable assembly of the embodiment of FIG. 6.

FIGS. 6, 7, 8 and 9 illustrate an alternative embodiment of the invention. A cable assembly 16 is provided with a clip mechanism to allow affixing of the cable assembly to the handpiece. In FIG. 7 an exploded side view of the cable assembly of the embodiment is shown. The figure shows a clip release version of the cable assembly having a primary coil construction. The primary coil 27 is wound on the primary bobbin 31 and covered with a protective outer casing 26 to protect the coils from fluid ingress and damage. A clip mechanism 28, housed in a clip casing 29, and through which the handpiece cable 15 passes is connected to the primary bobbin 31 through a primary washer 34 as shown in FIG. 8. A ferrite core 32 concentrates the flux to increase coupling to allow for the efficient transfer of power.

Figure 9:
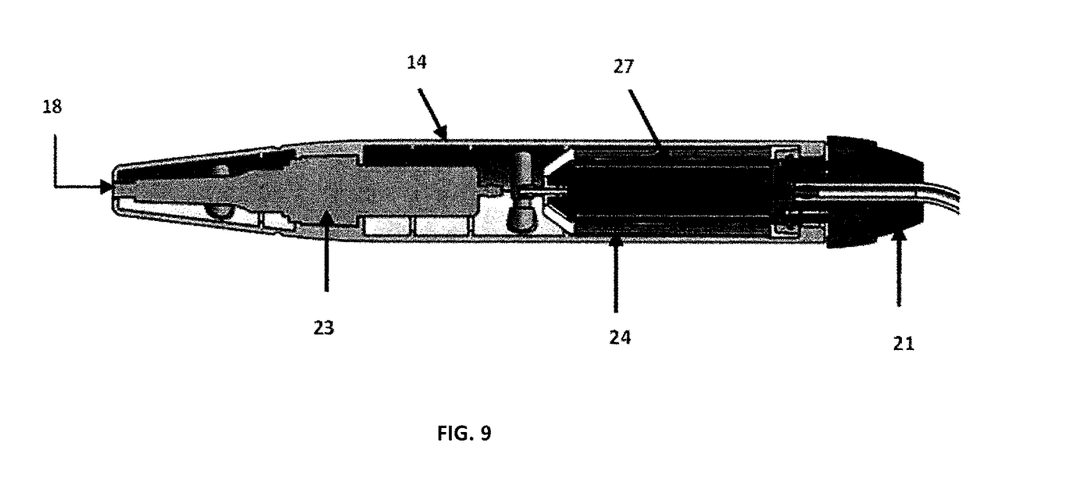
FIG. 9 is a cross sectional view of the alternative embodiment of FIG. 6 illustrating the location of the piezo assembly in relation to primary and secondary coils.
Figure 10:
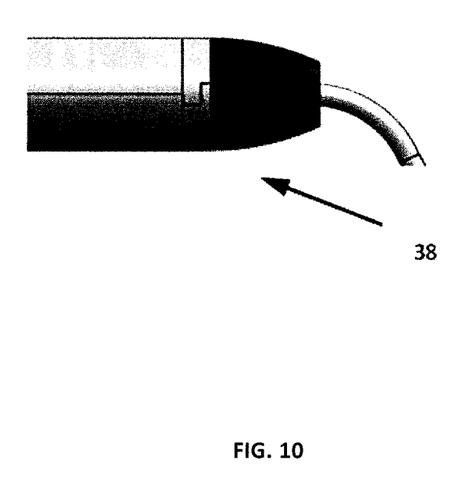
FIG. 10 illustrates a side view of a smooth ended cable assembly according to an embodiment of the present disclosure.
Figure 11:
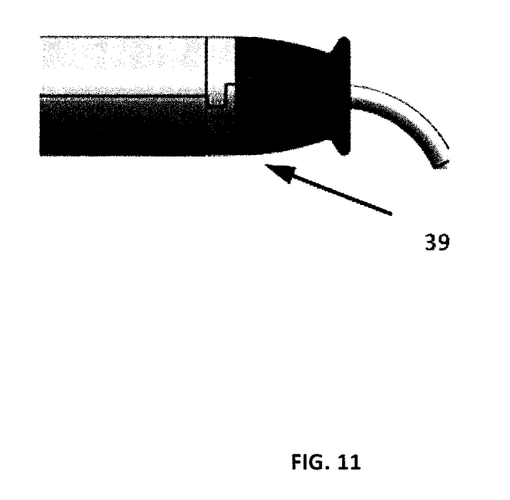
FIG. 11 illustrates a side view of a lipped cable assembly according to an embodiment of the present disclosure.

Referring to FIG. 9, a cross sectional view of the alternative embodiment of FIG. 6 illustrates the location of the piezo assembly 23 in relation to primary coil 27 and secondary coil 24. The mechanical working end of the piezo scaling tip (not shown) extends from the distal end 18 of the piezo assembly 23.

Figure 12:
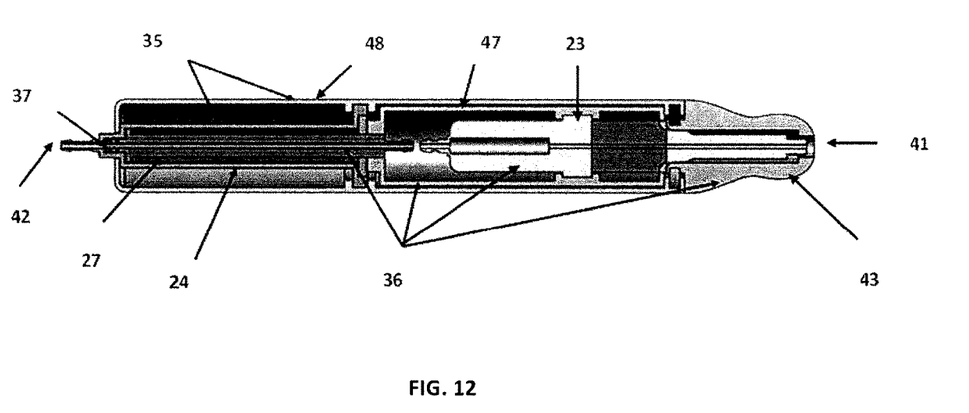
FIG. 12 shows a cross sectional view of an alternative embodiment according to the disclosure.

As shown in FIG. 12, an alternative embodiment of the invention comprises components that rotate with the piezo 36 which are mechanically or electrically connected to the cable. A rotary transformer is housed within the handpiece. A transducer 23 is fixed to the nose 43 at the distal 41 end of the handpiece such that the nose 43, transducer 23, inner housing 47 and primary coil 27 are movable components 36 and can rotate relative to the secondary coil 24 and outer housing 48 which are stationary components 35 of the handpiece. This allows the handpiece tip(not shown) to be oriented to the tooth(not shown) while rotating the nose 43, rotating fluid seal 37 located at the proximal end 42, and other rotating components 36 relative to the stationary components 35.

As shown in FIGS. 4, 5 and 8, the operation of a preferred embodiment of the handpiece involves providing the piezoelectric elements 8 with energy that causes the elements to flex. This movement results in vibrations in the mechanical working end of the piezo scaling tip(not shown) which is then applied on to the teeth. High vibrational energy created by the mechanical action of the tip crushes and removes calculus. Shockwaves and turbulence created disrupt bacterial cells and biofilms. The piezo transducer assembly 23 is electrically connected by wires 12, 13 to a secondary winding 24. A water tube (not shown) connects the fluid transferred from the primary bobbin 31 through the dynamic fluid interface 17 and into a water fitting 30 at the end of the secondary bobbin 33. The water tube then connects with a barb fitting 11 at the proximal end of the transducer assembly 23 located at the tail mass 9. The secondary coil 24 works in conjunction with the primary coil 27 to couple ultrasonic power. The primary coil 27 induces a voltage and current on the secondary coil that is used to energize the piezoelectric transducer. The secondary coil 24 and transducer are mechanically fixed in the same housing, such that the wires and tubing between the secondary coil and transducer only experience ambient ultrasonic vibration. When the handpiece is rotated relative to the cable assembly, the transducer 23, secondary coil 24, and handpiece 14 rotate as one assembly. The primary coil and dynamic fluid interface 17 are meant to slip inside the handpiece with very little frictional drag so that the operator can manipulate the ultrasonic tip without any torsional resistance from the handpiece cable 15 or the internal seals and bearings. The dynamic fluid interface 17 allows for the rotation of the primary coil relative to the secondary coil without seal leakage due to the use of the rotary coupling means. The rotary coupling features low friction materials, smooth finish and a small radius to reduce the frictional torque generated from the force of the interference fit.

In other embodiments, the secondary coil 24 may provide a power supply to electrical devices such as, but not limited to high speed rotary machines, low speed rotary machines, curing lights and caries detectors. A circuit to rectify the ultrasonic drive signal to provide DC power to energize a secondary circuit may be achieved. A tertiary coil may also be included with the secondary coil to provide a low voltage power source to energize integrated LED illumination common to piezoelectric scaling handpieces.

What has been described and illustrated herein is a preferred embodiment of the invention along with some of its variations. The terms, descriptions and figures used herein are set forth by way of illustration only and are not meant as limitations. Those skilled in the art will recognize that many variations are possible within the spirit and scope of the invention in which all terms are meant in their broadest, reasonable sense unless otherwise indicated. Any headings utilized within the description are for convenience only and have no legal or limiting effect.

INDEX OF ELEMENTS

1: Housing Tip
2: Housing Tip O-Ring
3: Housing
4: Connector O-Ring
5: Connector
6: Ultrasonic Horn
7: Solder Tab
8: Piezoelectric Element
9: Tail Mass
10: Tail Mass O-Ring
11: Metal Barb Fluid Fitting
12: 30AWG Red Wire
13: 30Awg Black Wire
14: Handpiece
15: Handpiece Cable
16: Cable Assembly
17: Dynamic Fluid Interface
18: Distal End of Handpiece
19: Smooth/Teflon/Grooved Bearing
20: Cable Assembly O-Ring
21: Rear Cap
22: Outer Casework
23: Piezo Assembly/Transducer
24: Secondary Coil/Winding
25: Fluid Swivel
26: Outer Casing
27: Primary Coil/Winding
28: Clip Mechanism
29: Clip Casing
30: Water fitting
31: Primary Bobbin
32: Ferrite Core
33: Secondary Bobbin
34: Primary Washer
35: Stationary Components
36: Components Rotating with Piezo
37: Rotating Fluid Seal
38: Smooth End Option
39: Lipped End Option
40: Primary Coil Coupling
41: Distal End of Handpiece
42: Proximal End of Handpiece
43: Nose
44: Moves with plug
45: Moves with hand piece
46: Flow of water
47: Inner Housing
48: Outer Housing
49: Dynamic Fluid Interface O-ring

The invention claimed is:

1. A dental handpiece assembly comprising:
a handpiece tip connected to a handpiece;
a handpiece housing of the handpiece enclosing a transducer assembly, the transducer assembly is in electrical communication with a secondary coil;
a cable assembly comprising a cable and a primary coil said cable assembly configured to be connected to said handpiece housing through a swivel mechanism;
a dynamic fluid interface between the cable assembly and the handpiece defined by a rotary connection between a primary bobbin of the primary coil and a water fitting of the handpiece, said water fitting disposed at an end of a secondary bobbin of the secondary coil, such that an arrangement of the dynamic fluid interface, the primary coil of the cable assembly and the secondary coil of the handpiece relative to each other produces the swivel mechanism so as to enable rotation of the primary coil relative to the secondary coil without seal leakage while unrestrictedly transmitting energy and lavage inside the handpiece, and
wherein the handpiece is decoupled from a torsional load applied to it by the cable assembly and internal tubing and wires.

2. The dental handpiece assembly of claim 1, wherein the transducer assembly is a piezo assembly.

3. The dental handpiece assembly of claim 1, wherein the cable assembly is configured to provide said lavage and electrical energy to the handpiece.

4. The dental handpiece assembly of claim 1, wherein the primary and secondary coils form a rotary transformer, wherein the secondary coil is inductively coupled to the primary coil.

5. The dental handpiece assembly of claim 4, further comprising a ferrite core for concentrating flux to increase coupling of the primary coil with the secondary coil.

6. The dental handpiece assembly of claim 4, wherein a turns ratio of the primary coil to the secondary coil is 1:1.

7. The dental handpiece assembly of claim 1, wherein the cable assembly is detachable from the handpiece housing.

8. The dental handpiece assembly of claim 1, wherein the handpiece is configured to be autoclavable.

9. The dental handpiece assembly of claim 1, wherein a water tube connects the lavage from the primary bobbin to the water fitting at the end of the secondary bobbin.

10. The dental handpiece assembly of claim 1, wherein the cable assembly has a rear cap that includes an o-ring configured to interlock with an inside diameter of a bearing disposed in the handpiece housing in order to secure the handpiece to the cable assembly.

11. The dental handpiece assembly of claim 1, wherein a fluid channel of the cable assembly engages a fluid channel of the primary bobbin through a primary washer.

* * * * *